(12) United States Patent
Kanno

(10) Patent No.: US 6,217,321 B1
(45) Date of Patent: Apr. 17, 2001

(54) ORTHODONTIC BRACKET

(76) Inventor: Yoneo Kanno, 5-181-96, Higashihatsuishi, Nagareyama-shi, Chiba (JP)

( * ) Notice: Subject to any disclaimer, the term of this patent is extended or adjusted under 35 U.S.C. 154(b) by 0 days.

(21) Appl. No.: 09/475,246

(22) Filed: Dec. 30, 1999

(30) Foreign Application Priority Data

Oct. 27, 1999 (JP) .................................................. 11-304833

(51) Int. Cl.[7] ...................................................... A61C 3/00
(52) U.S. Cl. .................................................. 433/11; 433/14
(58) Field of Search .................................. 433/11 O, 14, 433/20

(56) References Cited

U.S. PATENT DOCUMENTS

| 2,548,864 | * | 4/1951 | Brusse | 433/11 |
| 4,260,375 | * | 4/1981 | Wallshein | 433/11 |
| 5,908,293 | * | 6/1999 | Voudouris | 433/11 |

* cited by examiner

Primary Examiner—John J. Wilson
(74) Attorney, Agent, or Firm—Oblon, Spivak, McClelland, Maier & Neustadt, P.C.

(57) ABSTRACT

An orthodontic bracket is capable of smoothly performing an orthodontic operation without the need of any troublesome fastening operation, and securely fixes an orthodontic wire in slots by pressing the wire with a suitable magnitude of elastic force. The bracket includes a bracket body and a pressing spring. The bracket body has mounts provided on a base with a predetermined spacing therebetween in a facing fashion and also provided in the middle with slots. The bases of the mounts are formed with axial holes. Further, the pressing spring includes a pressing portion, which is provided at a central portion of the wire and has a length bridging the slots, and which is bent at both ends thereof in the same direction to bridge the slots. A pair to upright portions is formed at tip ends of the pressing portion to rise upright along outer sides of the slots. A pair of axial support portions is formed at tip ends of the upright portions to extend through the axial holes. A pair of latches is bent and formed at tip ends of the axial support portions to extend along the base in spacing.

3 Claims, 5 Drawing Sheets

ORTHODONTIC BRACKET

BACKGROUND OF THE INVENTION

1. Field of the Invention

The present invention relates to an orthodontic bracket.

2. Description of the Related Art

Conventional orthodontic brackets are generally well known, in which mounts each provided with a slot for receiving an orthodontic wire on the base thereof are so arranged as to face each other with a desired spacing therebetween, and each mount is provided on both sides thereof with projecting wings.

To fix the orthodontic wire using such a bracket, a length of ligature wire is applied across the orthodontic wire received in the slots to be trained around the underside of the wings to be tied.

Also, the inventor of the present application has filed an application on a constitution, in which a latch groove is provided outside of a base of a mount on a bracket, and a length of elastic wire is separately bent to form a pressing spring for fixation of an orthodontic wire in a slot. With the pressing spring, fixing portions on both ends of the spring are fixed to the base, bent portions provided contiguous to the fixing portions are held in the latch groove of the mount, and a pressing portion adapted to lie over the slot is formed from upright portions, which extend beyond the bent portions, and is used to elastically press the orthodontic wire.

An orthodontic bracket, which uses the above-described ligature wire to fasten an orthodontic wire in slots, requires a troublesome fastening operation, thus disadvantageously taking much time in an orthodontic operation.

Also, the bracket, which uses the above-described pressing spring and on which the inventor of the present application filed an application for patent, is of less utility because the bent portions of the pressing spring are liable to disengage from the latch groove and the fixing portions on both ends of the spring have to be fused to the base.

In light of the disadvantages of the prior art, the present invention provides an orthodontic bracket, which is capable of smoothly performing an orthodontic operation without the need of any troublesome fastening operation, and surely fixing an orthodontic wire in slots by pressing the wire with suitable elastic force.

SUMMARY OF THE INVENTION

To attain the above-described object, an orthodontic bracket, according to the present invention, comprises a bracket body and a pressing spring. The bracket body comprises mounts provided on a base with a predetermined spacing therebetween in a facing fashion and provided in the middle thereof with slots for receiving therein an orthodontic wire, the mounts being formed with axial holes, which are provided in the bases of the mounts to extend below the slots in the same direction as the slots do. Further, the pressing spring is formed by bending a wire and comprises a pressing portion, which is provided at the central portion of the spring and has a length bridging the two slots, and which is bent at both ends thereof in the same direction to bridge the two slots, upright portions formed at both ends of the pressing portion to rise upright along the outside of the slots, bent portions provided at the tip ends of the upright portions to extend along the underside of the slots, axial support portions formed at the tip ends of the bent portions to bend inward to extend through the axial holes, and latches formed at the tip ends of the axial support portions to extend along the base in the spacing in a direction, which enables the pressing portion to pressingly abut against the orthodontic wire in the slots.

Further, if the slots in the bracket body has a great depth, the axial holes may be provided to extend on one side of the slots in the bases of the mounts in the same direction as the slots do, and the tip ends of the upright portions on the pressing spring may be bent inward to directly form the axial support portions, which extend through the axial holes.

Further, in some cases, the bracket body comprises an auxiliary tube provided on one side of the base, mounts provided on the other side of the base with a spacing therebetween in a facing fashion, and a slot formed between the two mounts and the auxiliary tube to receive therein an orthodontic wire, two mounts being provided at the bases thereof with axial holes, which extend in the same direction as the slots do, and the tip ends of the upright portions on the pressing spring may be bent inward to form the axial support portions, which extend through the axial holes.

The orthodontic bracket, according to the present invention, comprises a bracket body and a pressing spring.

The bracket body comprises mounts provided on a base with a predetermined spacing therebetween in a facing fashion and provided in the middle thereof with slots for receiving therein an orthodontic wire. Wings are provided in the upper and outward portion of the respective mounts to protrude therefrom. The respective mounts are formed with axial holes, which are provided below the slots to extend in the same direction as the slots do.

Further, the pressing spring is formed by bending a round or rectangular wire, and comprises a pressing portion, which is provided at the central portion of the spring and has a length bridging the two slots, and which is bent at both ends thereof in the same direction to bridge the two slots, upright portions formed at both ends of the pressing portion to rise upright along the outside of the slots, bent portions provided at the tip ends of the upright portions to extend along the underside of the slots, axial support portions formed at the tip ends of the bent portions to bend inward to extend through the axial holes, and latches formed at the tip ends of the axial support portions. The latches are made stationary along the base in the spacing in a direction, in which the pressing portion can pressingly abut against an orthodontic wire in the slots.

Further, if the slots in the bracket body have a great depth, the axial holes may be provided to extend on one side of the slots in the bases of the mounts in the same direction as the slots do, and the tip ends of the upright portions on the pressing spring may be bent inward to directly form the axial support portions, which extend through the axial holes. In this case, no bent portions are provided between the upright portions and the axial support portions.

Further, the bracket body comprises an auxiliary tube provided on one side of the base, and mounts provided on the other side of the base with a spacing therebetween. The auxiliary tube may include a round tube and a rectangular tube. A slot is formed between the two mounts and the auxiliary tube to receive therein an orthodontic wire, the two mounts being provided at the bases thereof with axial holes, which extend in the same direction as the slots do. Wings are provided in the upper and outward portion of the respective mounts to protrude therefrom. In some cases, the tip ends of the upright portions on the pressing spring are bent inward to form axial support portions, which extend through the axial holes.

Other aspects and advantages of the present invention will become apparent from the following description, taken in conjunction with the accompanying drawings, illustrated by way of example of principles of the invention.

BRIEF DESCRIPTION OF THE DRAWINGS

The invention, together with objects and advantages thereof, may best be understood by reference to the following description of the presently preferred embodiments together with the accompanying drawings in which.

DESCRIPTION OF THE PREFERRED EMBODIMENTS

Figure 1:
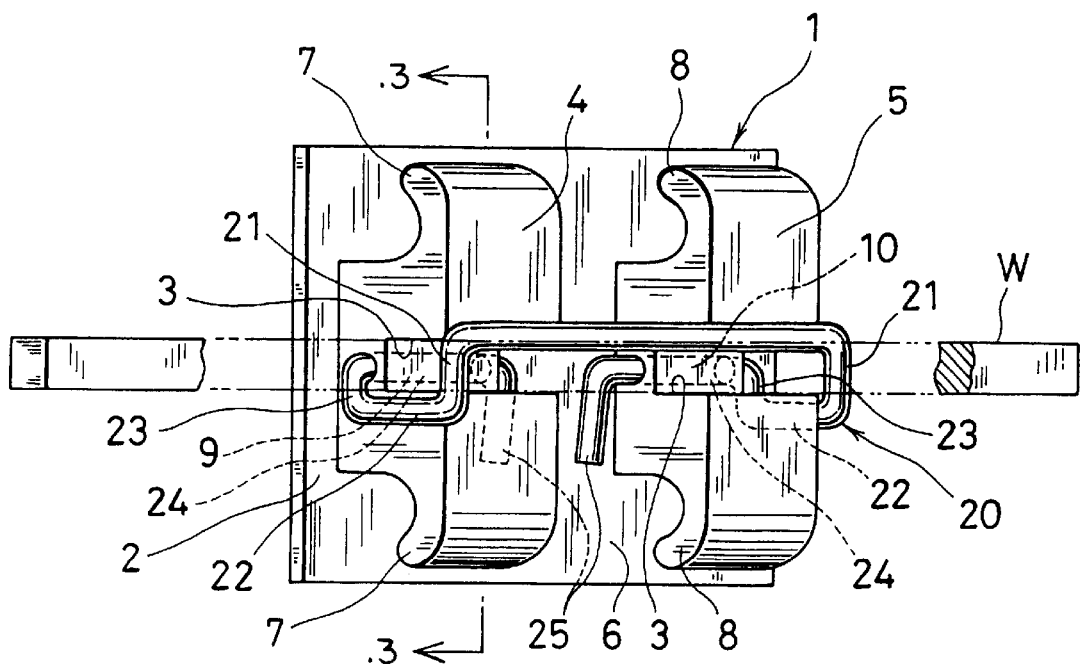
FIG. 1 is a perspective view showing a bracket in a first embodiment.
Figure 2:
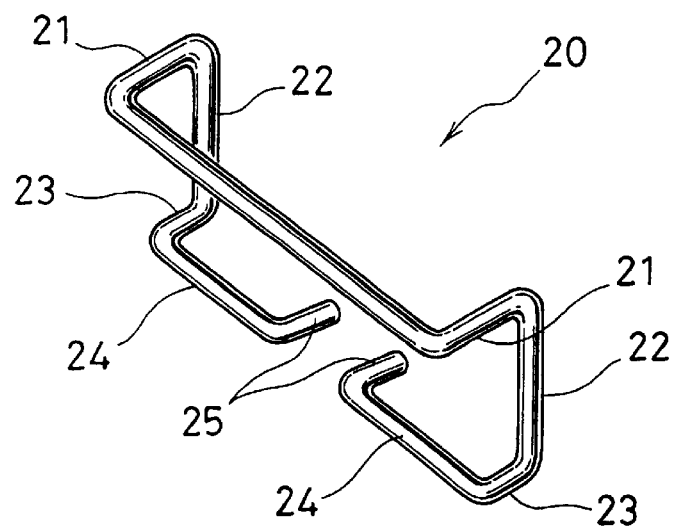
FIG. 2 is a perspective view showing a pressing spring.

An embodiment of the invention will be described hereinbelow with reference to the accompanying drawings.

First, in FIGS. 1 to 4, there is a bracket body 1. Concave-shaped mounts 4, 5 each provided at the middle thereof with a slot 3 for receiving therein an orthodontic wire are provided on a base 2 of the bracket body 1 in a facing fashion with a spacing 6 therebetween. Wings 7, 8 are provided integrally on an upper and outward portion of the respective mounts 4, 5 to protrude therefrom. Also, axial holes 9, 10 extending in the same direction as the slots do are provided below the slots in the bases of the respective mounts 4, 5.

A pressing spring 20iformed by bending a round wire having elasticity. A central portion of the pressing spring 20 has a length bridging the two slots 3, 3 and is bent at both ends thereof in the same direction to form pressing portions 21, 21 adapted to lie on the two slots 3, 3. The two pressing portions 21, 21, respectively, are formed at the tip ends (disposed on sides toward the tip ends of the wire) thereof with upright portions 22, 22, which rise along the outside of the slots 3, 3 and are provided at the tip ends thereof with bent portions 23, 23, which extend along the underside of the slots 3, 3. The bent portions 23, 23, respectively, are bent inward to be formed at the tip ends thereof with axial support portions 24, 24, which extend through the axial holes 9, 10 and are bent at the tip ends thereof to be formed with latches 25, 25. The respective latches 25, 25 are made stationary along the base 2 in the spacing 6 so that spring force applies in a direction, in which the pressing portions 21, 21 pressingly abut against an orthodontic wire W in the slots 3, 3, that is, a direction indicated by the arrow a in FIG. 3.

Thus, although the pressing spring 20 exhibits elastic force tending to have the two pressing portions 21 returning toward the slots 3 at all times, it is inhibited from disengaging from the bracket body 1 or rising from the base 2 because the axial support portions 24, 24 in FIG. 1 are extended through the axial holes 9, 10.

Now, operation of the orthodontic bracket of the present invention will be described below. When the orthodontic wire W is placed on the top surface of the mounts 4, 5 and brought into contact with the pressing portions 21 of the pressing spring 20 to be pushed in a direction indicated by the arrow b as shown in FIG. 3, the pressing spring 20 turns on both axial support portions 24, 24 in FIG. 4 against the elastic force to open the top portions of the slots 3, 3.

Figure 3:
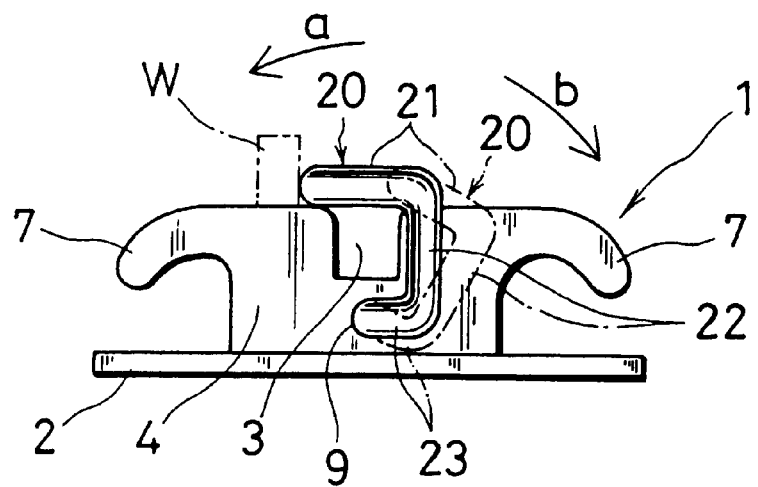
FIG. 3 is a side view showing the bracket.
Figure 4:
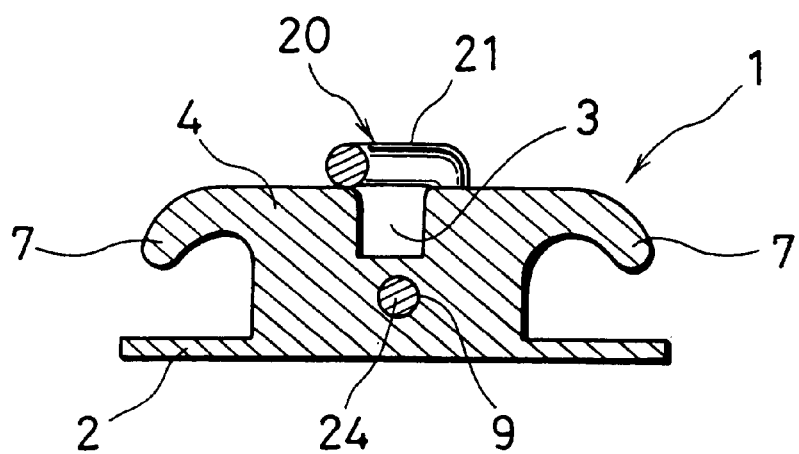
FIG. 4 is a cross-sectional view taken along the line A—A in FIG. 1.

Then, when pushed downward into the slots 3, 3, the orthodontic wire W in FIG. 3 is received in the slots 3, 3 and simultaneously the pressing spring 20 elastically returns above the slots 3, 3 to press the orthodontic wire W with the elastic force of the two pressing portions 21, 21.

Therefore, it is possible to fix the orthodontic wire W to the bracket body 1 without the use of a conventional binding operation with ligature wire.

Also, for disengagement of the orthodontic wire W, it is possible to instantaneously take out the orthodontic wire W from the slots 3 by pushing aside the pressing portion 21 by means of a tool, such as tweezers, in a direction shown by dashed lines in FIG. 3.

Figure 5:
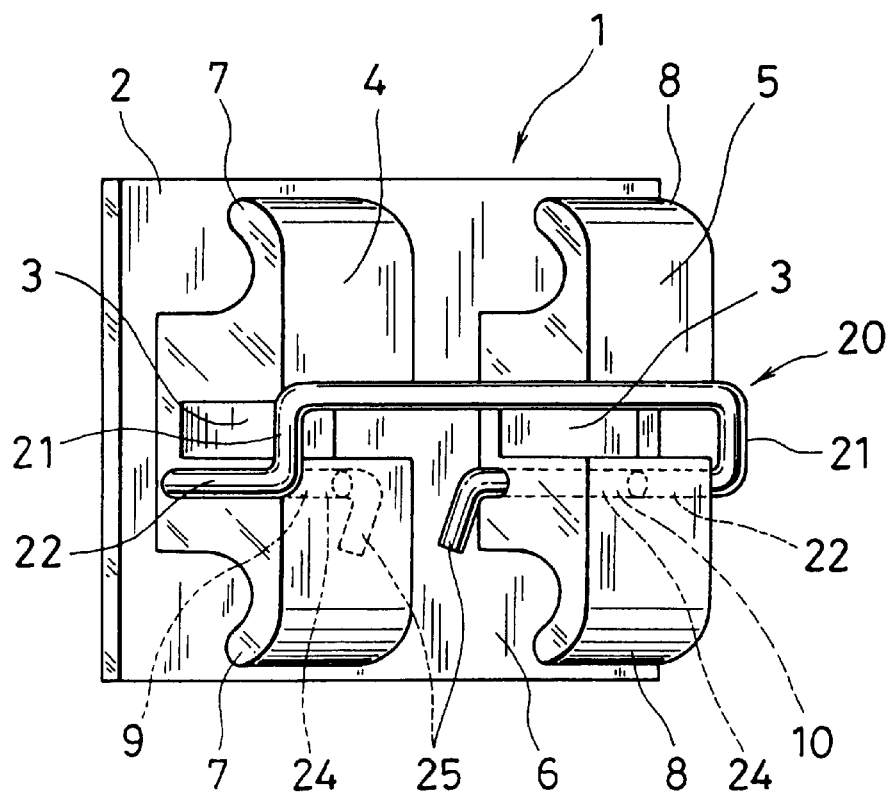
FIG. 5 is a perspective view showing a bracket in a second embodiment.
Figure 6:
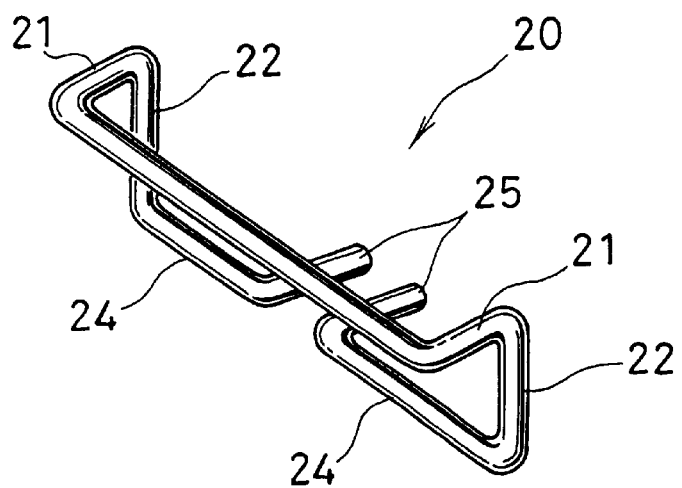
FIG. 6 is a perspective view showing a pressing spring.

In a second embodiment shown in FIGS. 5 and 6, slots 3 are formed to have a greater depth than that in the first embodiment. As shown in FIG. 5, respective mounts 4, 5, on the bracket body 1, in the bases thereof are formed with axial holes 9, 10, which are disposed on one side of the slots 3. Also, a pressing spring 20 is not provided with the bent portions 23 of the first embodiment, and the tip ends of two upright portions 22, respectively, are bent inward to form axial support portions 24, 24, which extend through axial holes 9, 10.

Thus, with this embodiment, the manner of fixing and disengaging of the orthodontic wire is the same as that in the first embodiment, so that the orthodontic wire can be surely fixed in the slots.

Figure 7:
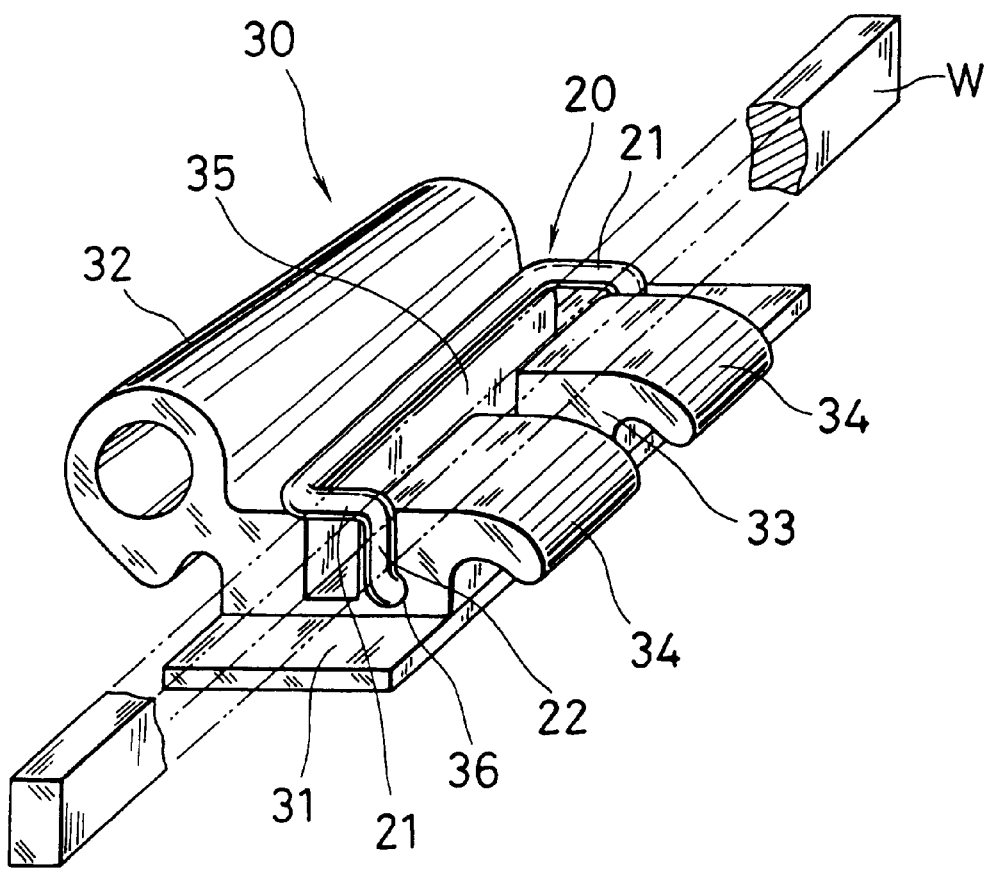
FIG. 7 is a perspective view showing a bracket in a third embodiment.
Figure 8:
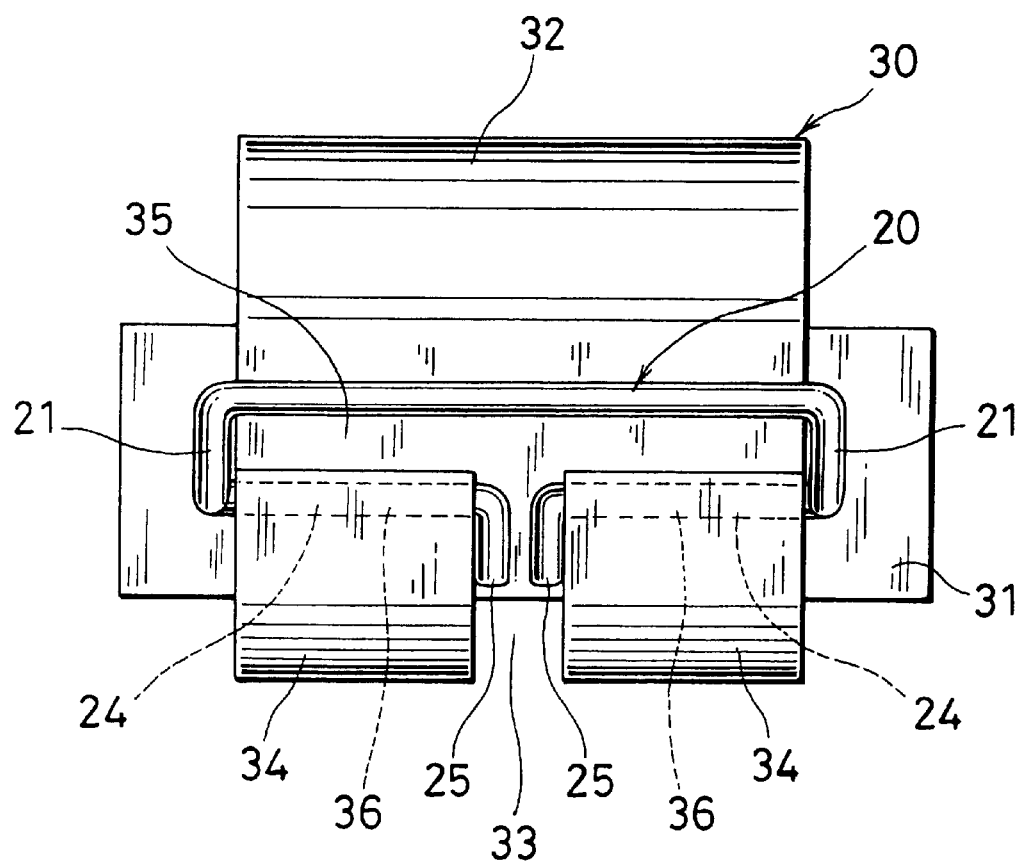
FIG. 8 is a plan view showing the bracket.

A third embodiment is an application to a buccal tube in an orthodontic bracket. In FIGS. 7 and 8, there is a bracket body 30 for buccal tubes, comprising a round buccal tube 32 provided on one side of a base 31, and mounts 34, 34 provided on the other side of the base 31 to face each other with a predetermined spacing 33 therebetween. Also, a slot 35 for receiving therein an orthodontic wire W is provided between the two mounts 34 and the tube 32, and an axial hole 36 is provided in bases 31 of the two mounts 34, 34 to extend in the same direction as the slot 35 does.

In this embodiment, a pressing spring 20 also has substantially the same shape as that in the second embodiment, and is mounted on the bracket body 30 in a similar manner as in the first embodiment.

Thus, in this embodiment, the orthodontic wire W can be surely fixed to the buccal tube 32 and easily be dismounted therefrom.

With the arrangement according to the present invention, an orthodontic operation can be smoothly performed since an orthodontic wire can be correctly mounted to a bracket without the need of a troublesome operation of binding the orthodontic wire in slots with a ligature wire.

Also, the orthodontic wire is pushed by high elastic force to be inhibited from disengaging from the bracket even if a tensile force applies on the orthodontic wire, so that an orthodontic operation can be performed safely.

The present examples and embodiments are to be considered as illustrative and not restrictive and the invention is not to be limited to the details given herein, but may be modified within the scope and equivalence of the appended claims.

What is claimed is:

1. An orthodontic bracket, comprising:

a bracket body; and a pressing spring; and said bracket body having mounts provided on a base with a predetermined spacing therebetween in a facing fashion and provided in a middle with slots configured to receive therein an orthodontic wire, said mounts being formed with axial holes which are provided in bases of the mounts to extend below the slots in the same direction as the slots do;

said pressing spring being formed by bending a wire and including, a pressing portion which is provided at a central portion of the pressing spring and has a length bridging the slots, and which is bent at both ends thereof in the same direction to bridge the slots, upright portions formed at both ends of the pressing portion to rise upright along outer sides of the slots, bent portions provided at tip ends of the upright portions to extend along an underside of the slots, axial support portions formed at tip ends of the bent portions to bend inwardly to extend through the axial holes, and latches bent and formed at tip ends of the axial support portions to extend along the base in the predetermined spacing between the mounts in a direction, which enables the pressing portion to pressingly abut against the orthodontic wire in the slots.

2. An orthodontic bracket comprising:

a bracket body; and a pressing spring;

said bracket body having mounts provided on a base with a predetermined spacing therebetween in a facing fashion and provided in a middle with slots configured to receive therein an orthodontic wire, said mounts being formed with axial holes which are provided in bases of the mounts to extend on one side of the slots in the same direction as the slots do;

said pressing spring being formed by bending a wire and including, a pressing portion which is provided at a central portion of the pressing spring and has a length bridging the slots, and which is bent at both ends thereof in the same direction to bridge the slots, upright portions formed at both ends of the pressing portion to rise upright along outer sides of the slots, axial support portions formed at tip ends of the upright portions to bend inwardly to extend through the axial holes, and latches bent and formed at tip ends of the axial support portions to extend along the base in the predetermined spacing between the mounts in a direction which enables the pressing portion to pressingly abut against the orthodontic wire in the slots.

3. An orthodontic bracket comprising:

a bracket body; and a pressing spring;

said bracket body having an auxiliary tube provided on one side of a base, mounts provided on an opposite side of the base with a spacing therebetween in a facing fashion, and a slot formed between the mounts and the auxiliary tube to receive therein an orthodontic wire, said mounts being provided at bases thereof with axial holes which extend in the same direction as the slot does;

said pressing spring being formed by bending a wire and including, a pressing portion which is provided at a central portion of the pressing spring and has a length bridging the slot, and which is bent at both ends thereof in the same direction to bridge the slot, upright portions formed at both ends of the pressing portion to rise upright along an outer side of the slot, axial support portions formed at tip ends of the upright portions to bend inwardly to extend through the axial holes, and latches bent and formed at tip ends of the axial support portions to extend along the base in the spacing between the mounts in a direction which enables the pressing portion to pressingly abut against the orthodontic wire in the slot.

* * * * *